(12) United States Patent
Syrjälä et al.

(10) Patent No.: US 12,727,832 B2
(45) Date of Patent: Sep. 8, 2026

(54) TECHNIQUES FOR OPTIMAL PARAMETER TUNING FOR A WEARABLE DEVICE

(71) Applicant: Oura Health Oy, Oulu (FI)

(72) Inventors: Juha-Pekka Syrjälä, Oulu (FI); Yogesh Pande, Oulu (FI)

(73) Assignee: Oura Health Oy, Oulu (FI)

( * ) Notice: Subject to any disclaimer, the term of this patent is extended or adjusted under 35 U.S.C. 154(b) by 704 days.

(21) Appl. No.: 17/967,512

(22) Filed: Oct. 17, 2022

(65) Prior Publication Data

US 2024/0122550 A1 Apr. 18, 2024

(51) Int. Cl.
*A61B 5/00* (2006.01)
*A61B 5/024* (2006.01)

(52) U.S. Cl.
CPC ........ *A61B 5/7275* (2013.01); *A61B 5/02416* (2013.01); *A61B 5/02438* (2013.01); *A61B 5/6802* (2013.01); *A61B 5/7221* (2013.01); *A61B 5/742* (2013.01); *A61B 5/6826* (2013.01)

(58) Field of Classification Search
CPC ..... A61B 5/7275; A61B 5/6802; A61B 5/742; A61B 5/02416; A61B 5/02438; A61B 5/7221
See application file for complete search history.

(56) References Cited

U.S. PATENT DOCUMENTS

2012/0179011 A1* 7/2012 Moon ...................... A61B 5/28 600/324
2016/0081567 A1* 3/2016 Nousiainen ........ A61B 5/02438 600/473
2017/0014081 A1* 1/2017 Schipper ............. A61B 5/6826
2022/0133241 A1* 5/2022 Jones .................. A61B 5/1032 600/485

OTHER PUBLICATIONS

Neuman (Neuman, M. R. "Biopotential Electrodes." The Biomedical Engineering Handbook: Second Ed. Joseph D. Bronzino; Boca Raton: CRC Press LLC, 2000) (Year: 2000).*

* cited by examiner

*Primary Examiner* — Pamela M. Bays
(74) *Attorney, Agent, or Firm* — ArentFox Schiff LLP

(57) ABSTRACT

Methods, systems, and devices for wearable device are described. A method may include acquiring first physiological data from a user during a first measurement interval using an optical channel of a wearable device, the optical channel comprising a light-emitting component and a photodetector, where the first physiological data is acquired using a first measurement profile. The method may include acquiring second physiological data from the user during a second measurement interval using the optical channel, the second measurement interval subsequent to the first measurement interval, where the second physiological data is acquired using a second measurement profile. The method may include comparing respective measurement quality metrics, respective power consumption metrics, or both, associated with the first measurement profile and the second measurement profile, and selecting the first or second measurement profile to be used to acquire additional physiological data during a third measurement interval using the optical channel.

14 Claims, 9 Drawing Sheets

Figure 8:
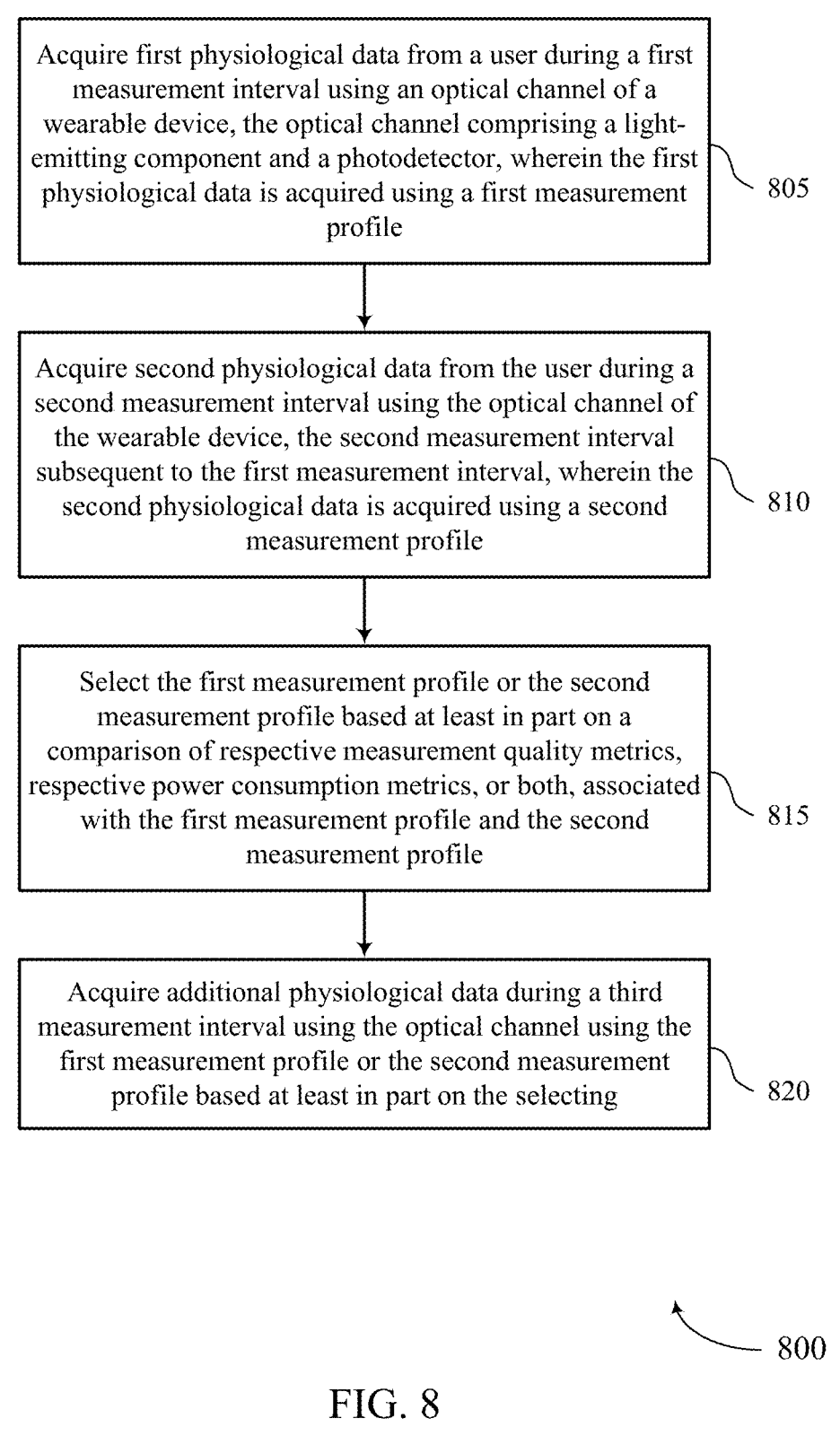

Acquire first physiological data from a user during a first measurement interval using an optical channel of a wearable device, the optical channel comprising a light-emitting component and a photodetector, wherein the first physiological data is acquired using a first measurement profile

805

Acquire second physiological data from the user during a second measurement interval using the optical channel of the wearable device, the second measurement interval subsequent to the first measurement interval, wherein the second physiological data is acquired using a second measurement profile

810

Select the first measurement profile or the second measurement profile based at least in part on a comparison of respective measurement quality metrics, respective power consumption metrics, or both, associated with the first measurement profile and the second measurement profile

815

Acquire additional physiological data during a third measurement interval using the optical channel using the first measurement profile or the second measurement profile based at least in part on the selecting

TECHNIQUES FOR OPTIMAL PARAMETER TUNING FOR A WEARABLE DEVICE

FIELD OF TECHNOLOGY

The following relates to wearable devices and data processing, including techniques for optimal parameter tuning for a wearable device.

BACKGROUND

Some wearable devices may be configured to collect data from users associated with heart rate of the user, such as motion data, temperature data, photoplethysmogram (PPG) data, etc. In some cases, some wearable devices may be configured to detect one or more sets of data under preconfigured conditions, and/or using preconfigured sets of components or measurement settings. Conventional techniques for detecting data in accordance with preconfigured conditions may be improved.

BRIEF DESCRIPTION OF THE DRAWINGS

FIG. 3 illustrates an example of a system that supports techniques for optimal parameter tuning for a wearable device in accordance with aspects of the present disclosure.

FIGS. 8 and 9 show flowcharts illustrating methods that support techniques for optimal parameter tuning for a wearable device in accordance with aspects of the present disclosure.

DETAILED DESCRIPTION

Figure 1:
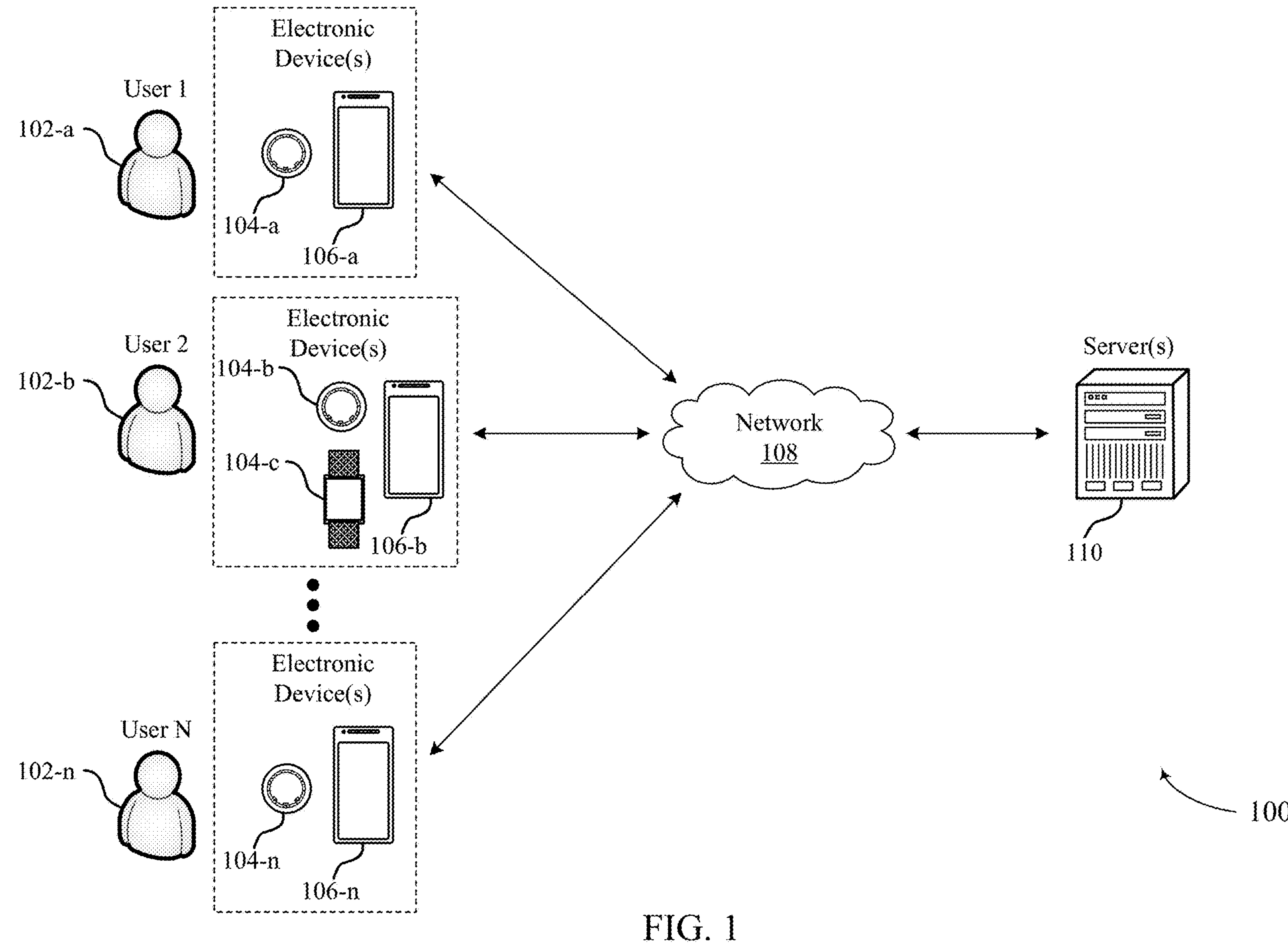
FIG. 1 illustrates an example of a system that supports techniques for optimal parameter tuning for a wearable device in accordance with aspects of the present disclosure.

Some wearable devices may be configured to collect data from users. For example, some wearable devices may be configured to continuously measure physiological data associated with a user including temperature data, heart rate data, and the like. As such, some wearable devices may be configured to house one or more sensors configured to collect physiological data from a user. In some cases, a wearable device may collect physiological data associated with a user using at least one optical channel, where the optical channel contains a photodetector and a light-emitting element. For example, the light-emitting element may emit light into a tissue surface of the user, and the photodetector may receive the emitted light that passes at least partially through the tissue surface. Accordingly, a user device associated with the wearable device may acquire physiological data from the user using the optical channel of the wearable device.

In some cases, a wearable device may be configured with various parameter or measurement settings, such as a voltage or current applied to the light-emitting component that is used to acquire physiological data. In some wearable devices, measurement settings/parameters may be predefined for each respective sensor and/or for each optical channel. That is, a light-emitting component may be configured to utilize a fixed voltage/current when emitting light to collect physiological data along a given optical channel.

However, the inability to adjust measurement parameters/settings for components of a wearable device may result in poor quality physiological data, increased power consumption (and therefore reduced battery life), or both. In particular, the measurement parameters for a given optical channel of a wearable device may affect the signal quality or power consumption of physiological data measurements collected from the user. For example, increasing the current/voltage applied to a light-emitting component may increase the signal quality of acquired physiological data, but may also increase the power consumption of the wearable device. A poor signal quality may detrimentally affect the ability of the wearable device to efficiently and accurately acquire physiological data, leading to a distorted picture of the user's overall health. Moreover, increased power consumption may lead to decreased battery life, and overall decreased user experience. In this regard, there may be a tradeoff between signal quality and power consumption when evaluating measurement parameters/settings for sensors of a wearable device.

Moreover, measurement parameters/settings for optical channels of a wearable device may not be "one size fits all." In other words, the measurement parameters may contribute to a signal quality and a power consumption level that is dependent on a particular human type (e.g., sex, weight, age, etc.), temperature (e.g., skin temperature), fit (e.g., ring tightness), environment, or some other characteristic. In this regard, predefined measurement parameters used for sensors of a wearable device may work for some users, but not for others.

Accordingly, to facilitate improved health monitoring, aspects of the present disclosure are directed to techniques for optical parameter tuning for a wearable device. In particular, techniques described herein may enable wearable devices to fine-tune measurement parameters (or "measurement profiles") that are used to acquire physiological data along a given optical channel.

For example, a wearable device may acquire physiological data from a user using an optical channel of a wearable device, where the optical channel includes a light-emitting component and a photodetector. In some implementations, the user device may use the optical channel to acquire first physiological data using a first measurement profile during a first measurement interval, and may use the same optical channel to acquire second physiological data using a second measurement profile during a second measurement interval. The first measurement profile and the second measurement profile may include respective sets of measurement parameters or settings associated with the light-emitting component, the photodetector, or both. The measurement parameters/settings associated with the respective measurement profiles may include a power level (e.g., voltage, current) associated with the light-emitting component, a burn time associated with the light-emitting component (e.g., how long the light-emitting component emits light to collect data), an analog-to-digital convertor range associated with the photodetector, a tuning algorithm, or a combination thereof.

Continuing with the same example, the wearable device may determine measurement quality metrics and/or power consumption metrics associated with the physiological data collected using the first and second measurement profiles. Based on a comparison of respective measurement quality metrics, respective power consumption metrics, or both, the wearable device may select one of the first or second measurement profiles. For instance, the wearable device may select the measurement profile associated with the higher measurement quality metrics and/or the lower power consumption metrics. The wearable device may then use the selected measurement profile to collect physiological data for the user. In some cases, the wearable device may test or evaluate multiple different measurement profiles for each respective optical channel of the wearable device to determine which measurement profile should be used for each respective optical channel, which measurement profile should be used under certain conditions, and the like.

Aspects of the disclosure are initially described in the context of systems supporting physiological data collection from users via wearable devices. Additional aspects of the disclosure are described in the context of an optical parameter tuning system. Aspects of the disclosure are further illustrated by and described with reference to apparatus diagrams, system diagrams, and flowcharts that relate to techniques for optimal parameter tuning for a wearable device.

FIG. 1 illustrates an example of a system 100 that supports techniques for optimal parameter tuning for a wearable device in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., ring 104-*a*) and a user device 106-*a* that may operate as described herein. In this example, the user device 106-*a* associated with user 102-*a* may process/store physiological parameters measured by the ring 104-*a*. Comparatively, a second user 102-*b* (User 2) may be associated with a ring 104-*b*, a watch wearable device 104-*c* (e.g., watch 104-*c*), and a user device 106-*b*, where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more LEDs (e.g., red LEDs, green LEDs) that emit light on the palm-side of a user's finger to collect physiological data based on arterial blood flow within the user's finger. In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time that the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g., in a hypothetical culture with 12 day "weeks", 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques that enable optimal parameter tuning for a wearable device 104. For example, a user device 106 may be associated with a wearable device 104 including an optical channel that includes a light-emitting component (e.g., an LED) and a photodetector. The wearable device 104 may use the optical channel of the wearable device to acquire physiological data.

In some implementations, the wearable device 104 may test different measurement profiles for a same optical path in different measurement intervals in order to select the optimal measurement profile for the optical channel of the wearable device 104. For example, the wearable device 104 may acquire first physiological data from a user during a first measurement interval using the optical channel, where the first physiological data is acquired using a first measurement profile. Additionally, the wearable device 104 may acquire second physiological data from the user during a second measurement interval using the optical channel, where the second physiological data is acquired using a second measurement profile.

Continuing with the same example, the wearable device 104 may compare respective measurement quality metrics, respective power consumption metrics, or both, associated with the first measurement profile and the second measurement profile, and may select one of the first or second measurement profiles that will be used for data collection in subsequent time intervals. In such implementations, the wearable device 104 may select a measurement profile that provides improved signal quality, reduced power consumption, or both, as described herein.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
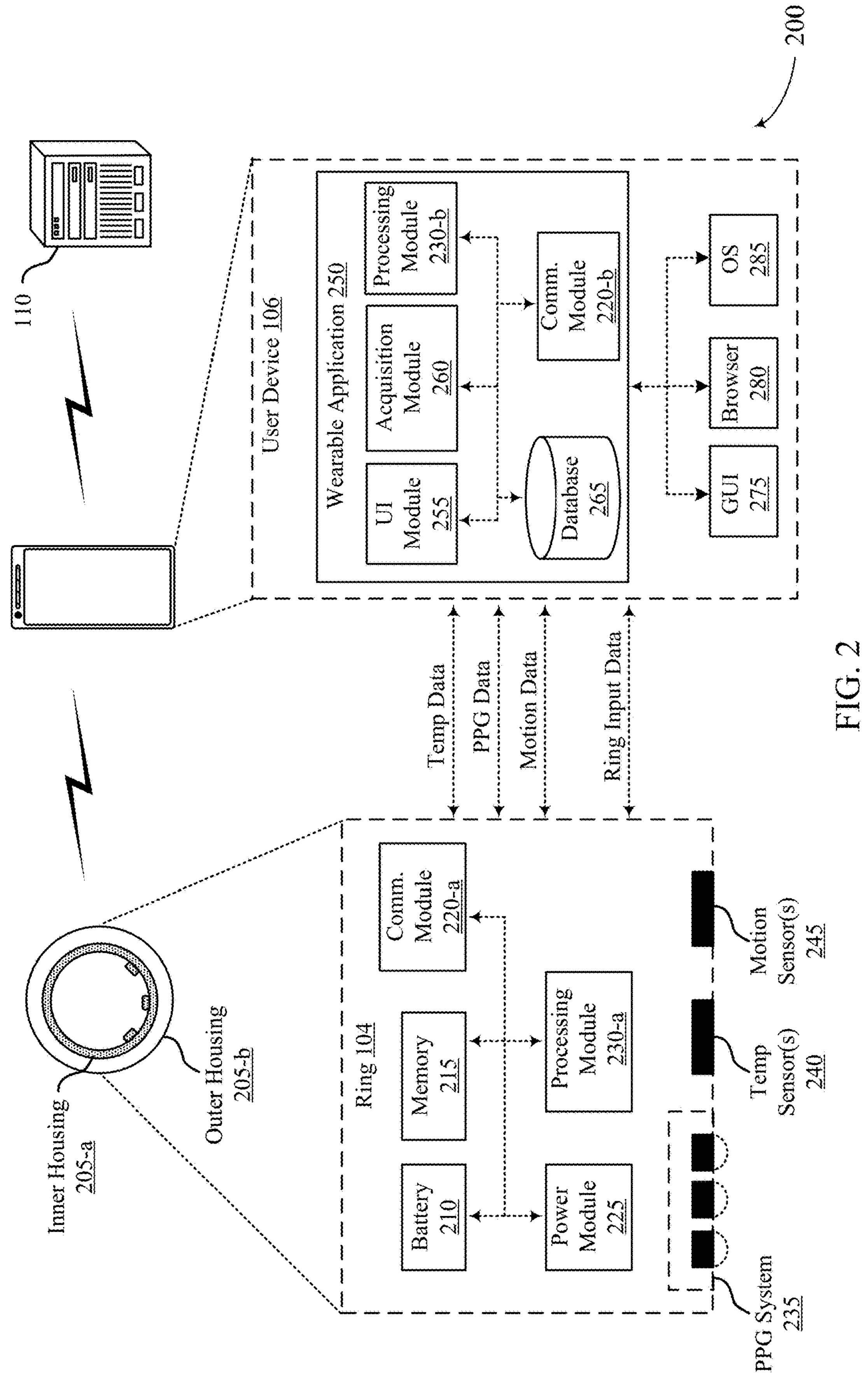
FIG. 2 illustrates an example of a system that supports techniques for optimal parameter tuning for a wearable device in accordance with aspects of the present disclosure.

FIG. 2 illustrates an example of a system 200 that supports techniques for optimal parameter tuning for a wearable device in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-*a* and an outer housing 205-*b*. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-*a*, a memory 215, a communication module 220-*a*, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-*b* component (e.g., a shell) and an inner housing 205-*a* component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate (s) from water and/or other chemicals.

The outer housing 205-*b* may be fabricated from one or more materials. In some implementations, the outer housing 205-*b* may include a metal, such as titanium, that may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG light emitting diodes (LEDs). In some implementations, the inner housing 205-*a* component may be molded onto the outer housing 205-*b*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the number of stored values. In a specific example, if average temperatures for a user over one minute are stored in memory 215, the processing module 230-*a* may calculate average temperatures over a five minute time period for storage, and then subsequently erase the one minute average temperature data. The processing module 230-*a* may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support techniques for optical parameter tuning for a wearable device 104 based on comparing various measurement profiles and/or power consumption metrics for an optical channel used to acquire physiological data of a user. In other words, techniques described herein may be used to select measurement profiles that will be used by respective optical channels to acquire physiological data.

For example, the wearable device 104, user device 106, and servers 110 of the system 200 may be configured to acquire physiological data from a user using an optical channel of the wearable device 104, the optical channel including a light-emitting component and a photodetector. In some implementations, the wearable device 104 may use the same optical channel to acquire physiological data using different measurement profiles during different measurement intervals (e.g., measurement slots). Each measurement profile may include or be associated with a combination of algorithms, parameters, control settings, and/or other pre-configured characteristics associated with the light-emitting component, the photodetector, or both. For example, an optical channel may be configured to collect physiological data using a first measurement profile and a second measurement profile. In this example, the first measurement profile may be associated with a first voltage/current applied to an LED of the optical channel, and the second measurement profile may be associated with a second voltage/current applied to the LED of the optical channel. By comparing measurement quality metrics and/or power consumption metrics associated with the measurement profiles, the user device 106 may select one of the measurement profiles to be used for subsequent physiological measurements.

For example, as noted previously herein, the wearable device 104 of the system 200 may be worn by a user to collect physiological data from the user. In some aspects, the wearable device 104 may acquire first physiological data from the user during a first measurement interval using a first measurement profile associated with the optical channel of the wearable device. Additionally, the user device 106 may acquire second physiological data from the user during a second measurement interval using a second measurement profile associated with the same optical channel. The second measurement profile may be the same or different from the first measurement profile. For instance, the second measurement profile may define a power level associated with the light-emitting component, a burn time associated with the light-emitting component, an ADC converter range associated with the photodetector, and/or a tuning algorithm that is different from that of the first measurement profile.

Continuing with the same example, the wearable device 104 may select the first measurement profile or the second measurement profile based on a comparison of respective measurement quality metrics, respective power consumption metrics, or both, associated with the physiological data collected according to the first measurement profile and the second measurement profile. Based on the selecting, the user device 106 may acquire additional physiological data during a third measurement interval using the optical channel using the first measurement profile or the second measurement profile.

In some cases, the wearable device 104 may test out different measurement profiles based on the user indicating that there is an issue with the physiological data collected by the wearable device 104. Additionally, or alternatively, the user device 106 may test out different measurement profiles based on a quality of physiological data failing to satisfy a quality threshold. The procedure for optical parameter tuning may be further shown and described with reference to FIG. 3.

Figure 3:
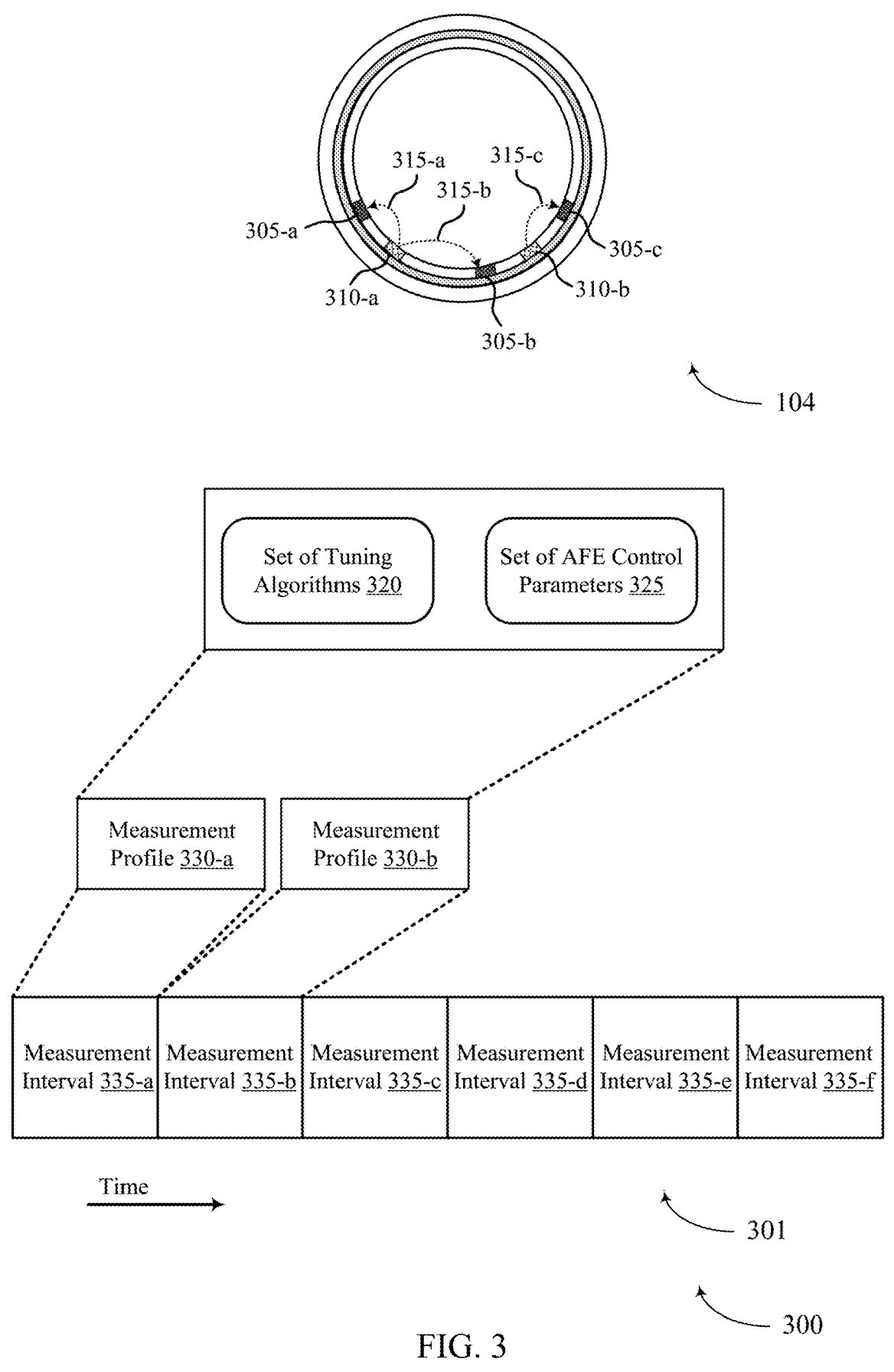

FIG. 3 illustrates an example of a system 300 that supports techniques for optimal parameter tuning for a wearable device in accordance with aspects of the present disclosure. Aspects of the system 300 may implement, or be implemented by, aspects of the system 100, the system 200, or both.

The system 300 illustrates a wearable device 104 and a measurement configuration 301, where the measurement configuration 301 may be implemented by the wearable device 104 to perform optimal parameter tuning.

In some aspects, the wearable device 104 may include one or more photodetectors 305, such as a photodetector 305-*a* (e.g., PD1), a photodetector 305-*b* (e.g., PD2), and a photodetector 305-*c* (e.g., PD3), and one or more light-emitting components (e.g., LEDs 310), such as an LED 310-*a* (e.g., LED1) and an LED 310-*b* (e.g., LED2), among other electronic components. In some cases, a set of photodetectors 305, a set of LEDs 310, or both, may be located at respective radial positions within an inner circumference (e.g., inner circumferential surface) of the wearable device 104.

In some examples, a user device (e.g., a user device 106) may acquire physiological data via the wearable device 104 (e.g., a wearable ring device) based on arterial blood flow, capillary blood flow, arteriole blood flow, or a combination thereof. In particular, in some implementations, the wearable device 104 may be configured to acquire physiological data using one or more optical channels 315, where each optical channel includes at least one LED 310 and at least one photodetector 305.

For example, as shown in FIG. 3, the wearable device 104 may include an optical channel 315-*a* including the LED 310-*a* and the photodetector 305-*a*, an optical channel 315-*b* including the LED 310-*a* and the photodetector 305-*b*, and an optical channel 315-*c* including the LED 310-*b* and the photodetector 305-*c*. It is noted herein that the wearable device 104 may include any quantity of optical channels 315 across any quantity of LEDs 310 and photodetectors 305.

In some aspects, the LED 310-*a* and the LED 310-*b* of the wearable device may be configured to emit light on the palm-side of a user's finger, and the photodetector 305-*a*, the photodetector 305-*b*, and the photodetector 305-*c* may receive, from the user's finger, the emitted light. As such, the wearable device 104 may use the optical channels 315 to collect physiological data of the user 102. In some cases, each of the optical channels 315 may contain one or more light-emitting components, one or more photodetectors, and/or one or more other components.

In some implementations, some of the sensors (e.g., photodetectors 305, LEDs 310) of the wearable device 104 may be positioned on/within the wearable device 104 symmetrically with respect to an axis of the wearable device 104, where at least one sensor (e.g., photodetector 305-*b*) is positioned asymmetrically with respect to the axis and/or the other sensors. For example, as shown in FIG. 3, the second photodetector 305-*b* may be positioned asymmetrically with respect to an axis of the wearable device 104, such that the second photodetector 305-*b* is positioned closer (e.g., radially, and linearly) to the second LED 310-*b* as compared to the first LED 310-*a*. The radial position of the photodetector 305-*b* may enable the wearable device 104 to support different lengths for the plurality of optical channels 315. For example, light emitted from the LED 310-*a* may travel along an optical channel 315-*a* to the photodetector 305-*a*, along an optical channel 315-*b* to the photodetector 305-*b*, and along an optical channel 315-*c* to the photodetector 305-*c*.

In some cases, wearable device 104 may use the optical channels 315 to acquire physiological data via different measurement profiles 330 during different measurement intervals 335 (e.g., measurement slots), where each of the measurement profiles 330 include a combination of algorithms (e.g., tuning algorithms 320), parameters (e.g., analog front-end (AFE) control parameters 325), control settings, and/or other preconfigured characteristics associated with the LED 310 of the optical channel 315, the photodetector 305 of the optical channel 315, or both. By comparing measurement quality metrics and/or power consumption metrics associated with the measurement profiles 330, the wearable device 104 may select one of the measurement profiles 330 to be used for subsequent physiological measurements.

For example, as shown in FIG. 3, the wearable device 104 may acquire first physiological data from the user 102 using the optical channel 315-*a* during a first measurement interval 335-*a*, where the first physiological data is acquired using a first measurement profile 330-*a*. Additionally, the wearable device 104 may acquire second physiological data from the user 102 using the optical channel 315-*a* during a second measurement interval 335-*b*, where the second physiological data is acquired using a second measurement profile 330-*b*. In this example, the wearable device 104 may determine measurement quality metrics, power consumption metrics, or both, associated with the data collection using the first and second measurement profiles 330. Based on a comparison of respective measurement quality metrics, respective power consumption metrics, or both, the wearable device 104 may select one of the first measurement profile 330-*a* or the second measurement profile 330-*b* that will be used for subsequent data collection.

For instance, if the wearable device 104 determines that the first measurement profile 330-*a* is associated with a higher measurement quality, a lower power consumption, or both, the wearable device 104 may select the first measurement profile 330-*a*, and may collect physiological data along the optical channel 315-*a* according to the first measurement profile 330-*a* for subsequent measurement intervals 335 (e.g., measurement intervals 335-*c*, 335-*d*, 335-*e*, 335-*f*). In some cases, measurement intervals 335 may also be referred to as measurement slots.

In some aspects, the measurement intervals 335 may be relatively short such that physiological data collected during subsequent measurement intervals 335 is effectively collected with the "same" physiological conditions (e.g., approximately the same blood flow, temperature, etc.), despite being collected at different times. For example, in some cases, the measurement intervals 335 may span a duration of 7 ms to 117 ms. With such short measurement intervals 335, physiological data collected during consecutive measurement intervals 335 may effectively capture the same "snapshots" of the user's physiological conditions (despite being taken at slightly different times), with the primary difference being the different measurement profiles 330 that are used.

Additionally, or alternatively, the wearable device 104 may test out different measurement profiles 330 for different optical channels 315 in different measurement intervals 335. In other words, the wearable device 104 may evaluate multiple different measurement profiles 330 for each respective optical channel 315 in order to determine which measurement profile 330 should be used for each respective optical channel 315.

For example, the wearable device 104 may acquire third physiological data from the user 102 using the optical channel 315-*b*, where the third physiological data is acquired using a third measurement profile 330. Additionally, the wearable device 104 may acquire fourth physiological data from the user 102 using the optical channel 315-*b*, where the fourth physiological data is acquired using a fourth measurement profile 330. Based on a comparison of respective measurement quality metrics, respective power consumption metrics, or both, associated with the third measurement profile 330 and the fourth measurement profile 330, the wearable device 104 may select the third measurement profile or the fourth measurement profile. In accordance with the selection made, the wearable device 104 may acquire fifth physiological data using the optical channel 315-*b* using the third measurement profile 330 or the fourth measurement profile 330.

In some examples, each of the optical channels 315 may be associated with a set of candidate measurement profiles 330 that the wearable device 104 may test. For example, the optical channel 315-*a* may be associated with the first measurement profile 330-*a* and the second measurement profile 330-*b*, and the optical channel 315-*b* may be associated with the third measurement profile 330 and the fourth measurement profile 330. By way of another example, each optical channel 315 may be associated with three or more measurement profiles 330 (e.g., five measurement profiles 330, ten measurement profiles 330, etc.). In other words, the wearable device 104 may be configured to "learn" which measurement profiles 330 are likely to result in high signal quality and/or low power consumption for each respective optical channel 315.

In some aspects, each measurement profile 330 may be associated with measurement parameters associated with components (e.g., LED 310, photodetector 304) of the respective optical channel 315. Moreover, each measurement profile may be associated with a set of measurement parameters, where the measurement parameters include a subset of tuning algorithms of a set of tuning algorithms 320 associated with the wearable device 104, and a subset of AFE control parameters 325 of a set of AFE control parameters 325 associated with the wearable device 104. Tuning algorithms 320 may include algorithms and computational settings associated with how physiological data is collected and processed according to the respective measurement profile 330 for a given optical channel 315.

The AFE control parameters 325 may include measurement settings associated with the LED 310 and/or photodetector 305 of a respective optical channel 315. For example, the AFE control parameters 325 of the wearable device 104 may include a power level associated with a light-emitting component (e.g., LED 310 power level), a burn time associated with the light-emitting component (e.g., LED 310 burn time), an analog-to-digital converter range associated with the photodetector 305 (e.g., sensitivity of the photodetector 305), or any combination thereof.

In some implementations, a user device 102 may send the set of tuning algorithms 320 and any associated tuning algorithm setting to the wearable device 104 so that the wearable device 104 may implement or apply the respective tuning algorithms 320 in the context of different measurement profiles 330. For example, the set of tuning algorithms 320 may be associated with a first tuning algorithm setting and a second tuning algorithm setting. In some examples, the wearable device may learn user device-specific or hardware-specific settings for data acquisition based on the set of tuning algorithms 320 and the associated tuning algorithm settings. For instance, the wearable device 104 may learn to use the first tuning algorithm setting for a first measurement scenario (e.g., for temperature data acquisition) and to use the second tuning algorithm setting for a second measurement scenarios (e.g., for movement data acquisition) based on device-specific or hardware-specific settings.

Upon testing out and comparing different measurement profiles 330 for a given optical channel, the wearable device 104 may select a measurement profile 330 that will be used for subsequent data collection. After selecting the measurement profile 330 for a given optical channel 315, the wearable device 104 may collect physiological data along the optical channel 315 using the selected measurement profile 330, and may display the physiological data acquired using the selected measurement profile 330. For instance, a GUI of the user device 106 may display an indication of the physiological data acquired using the selected measurement profile 330.

In some examples, the user device 106 may receive, from the wearable device 104, a message indicating which measurement profile 330 has been selected. For example, as shown in FIG. 3, the wearable device 104 may collect physiological data using an optical channel 315 during a first measurement interval 335-*a* and a second measurement interval 335-*b* using a first measurement profile 330 and a second measurement profile 330-*b*, respectively. In this example, the wearable device 104 may select the first measurement profile 330-*a* or the second measurement profile 330-*b* based on comparing measurement quality metrics, power consumption metrics, or both, associated with the respective measurement profiles 330. Subsequently, the wearable device 104 may send a message to the user device 106 indicating which measurement profile 330 was selected.

In this regard, the user device 106 may also be able to "learn" which measurement profiles 330 are used for respective optical channels 315, and under certain circumstances (e.g., first measurement profile 330-*a* may be better when the user exhibits higher skin temperature, where the second measurement profile 330-*b* may be better in high-motion scenarios). As will be described in further detail herein, the wearable device 104 may be configured to "test" or evaluate different measurement profiles 330 for each optical channel 315 at regular or irregular intervals, when certain conditions are satisfied (e.g., when a quality of physiological data collected using the current measurement profile 330 drops below a threshold, when a power consumption of the current measurement profile exceeds a threshold, etc.).

For example, in some cases, the wearable device 104 and/or the user device 106 may be configured to "learn" that, for a given optical channel 315, the second measurement profile 330-*b* is better suited for high temperature and high movement conditions as compared to the first measurement profile 330-*a*. In this example, the wearable device 104 may be configured to automatically switch to the second measurement profile 315-*b* when the wearable device 104 detects high temperature readings (e.g., temperature above a threshold) and high motion/acceleration readings (e.g., movement/acceleration above a threshold). In this regard, aspects of the present disclosure may enable the wearable device 104 to switch between different measurement profiles 330 for a given optical channel 315 based on one or more physiological parameters, such as heart rate, temperature, respiration rate, movement/acceleration, blood oxygen saturation, and the like.

In some cases, a user device 106 may perform a firmware update on the wearable device 104 to modify the measurement profiles 330, tuning algorithm settings associated with the set of tuning algorithms 320, or both. In some aspects, a user may trigger the firmware update on the wearable device 104. For example, if the user device 106 associated with the wearable device 104 receives a user input indicating an issue associated with the physiological data collected by the wearable device 104, the user device 106 may perform a firmware update to modify the tuning algorithm settings and/or measurement profiles 330.

Additionally, or alternatively, the user device 106 may transmit, to the wearable device 104 and based on the user input, a message indicating one or more measurement profiles 330, where the wearable device 104 acquires physiological data using the received measurement profiles 330. As such, the user may submit complaints if the wearable device 104 is not working correctly, and the user device 106 may send measurement profiles 330 to the wearable device 104 so that the wearable device 104 can test out different measurement profiles 330. In some examples, the user device 106 may send a request to customer services or a manufacturer of the wearable device 104 to modify the settings of the wearable device 104 (e.g., modify tuning algorithms, measurement profiles 330, etc.), and customer services or the manufacturer may send parallel algorithm settings (e.g., tuning algorithm settings) to the wearable device so that the outputs of the various tuning algorithm settings associated with the set of tuning algorithms 320 could be compared.

In other words, user devices 106 may be configured to "learn" which tuning algorithms and/or measurement profiles 330 are good for collecting data in certain circumstances and/or for certain people (e.g., different skin tones, different levels of movement/activity, different temperatures), and may "share" these tuning algorithms/measurement profiles 330 with other user devices 106 and wearable devices 104. For example, referring to FIG. 1, different user devices 106 may transmit measurement profiles 330 and corresponding characteristics (e.g., skin temperature, skin tone, activity, etc.) to the servers 110 so that the measurement profiles 330 may be maintained at the servers 110. In this example, if user's transmit complaints that their wearable device 104 is not collecting data properly, the server

110 may be configured to push different measurement profiles 330 to the wearable device 104 (for example, based on user's skin temperature, skin tone, etc.) to help resolve the issue.

In some aspects, the wearable device 104 and/or user device 106 may send the respective measurement quality metrics, the respective power consumption metrics, or both, associated with measurement profiles 330 back to the cloud (e.g., servers 110) where a comparison may be made. Accordingly, the one or more servers 110 may be configured to determine how different measurement parameters 330 (e.g., different measurement parameters, such as tuning algorithms 320 and/or control parameters 325) affect signal quality or lead to different outcomes with different people (e.g., wide population). In some examples, this data can then be compared with other characteristics collected from other users. Optimal parameters for a particular human type, ring tightness, or some other characterization could thus be found.

In additional or alternative implementations, the user device 104 may autonomously test out different measurement profiles 330 upon determining that the optical channel 315 is not collecting sufficiently high-quality data. For example, the wearable device 104 may determine that a quality of physiological data acquired by the wearable device 104 via the optical channel 315 fails to satisfy a quality threshold. In this example, the wearable device 104 may begin testing other measurement profiles 330 based on determining that the quality of the physiological data fails to satisfy the quality threshold. In some cases, the quality threshold may be preconfigured for the wearable device 104, the user device 104, and/or the user.

In some cases, the wearable device 104 may be configured to filter out or otherwise compensate for ambient light detected by the photodetectors 305. Compensating for ambient light may result in higher quality physiological data which is more representative of the user's physiological characteristics. For the purposes of the present disclosure, the term "ambient light" may include any light received by the photodetectors 305 that is not attributable to light transmitted by an LED 310. Thus, ambient light may refer to artificial indoor lighting (e.g., lamps, office lighting, sunlight, and the like).

For example, the wearable device 104 may measure a first ambient light level associated with the first measurement interval 335-*a* and a second ambient light level associated with the second measurement interval 335-*b*. In some aspects, the first ambient light level, the second ambient light level, or both, may include ambient light measurements at a beginning or end of the measurement interval 335-*a* and the measurement interval 335-*b*, respectively. Additionally, or alternatively, the first ambient light level, the second ambient light level, or both may include average ambient light measurements throughout the measurement interval 335-*a* and the measurement interval 335-*b*, respectfully.

Continuing with the same example, the wearable device 104 (or the user device 106 associated with the wearable device 104) may modify the physiological data collected during the respective measurement intervals 335 with the ambient light measurements performed during the respective measurement intervals 335. For instance, the wearable device 104 may modify the first physiological data collected during the first measurement interval 335-*a* based on the first ambient light level, and may modify the second physiological data collected during the second measurement interval 335-*b* based on the second ambient light level. In this example, the wearable device 104 may select one of the first measurement profile 330-*a* or the second measurement profile 330-*b* based on the modified physiological data.

In some examples, the wearable device 104 may perform ambient light cancellation by filtering or removing an ambient light level from a signal generated by a photodetector 305 during a measurement interval 335. For instance, the wearable device 104 may subtract the first ambient light level from a first signal generated by the photodetector 305 during the first measurement interval 335-*a*, and may subtract the second ambient light level from a second signal generated by the photodetector 305 during the second measurement interval 335-*b*.

In some implementations, a wearable device 104 may test out different measurement profiles 330 for different optical channels 315 to select the best measurement profile 330 for each respective optical channel 315 (or a measurement profile 330 which achieves a threshold measurement quality or threshold power consumption). For example, the wearable device 104 may test/compare a first set of measurement profiles 330 for the first optical channel 315-*a*, and may test/compare a second set of measurement profiles 330 for the second optical channel 315-*b*. In this example, the first and second sets of measurement profiles may be the same or different. In other words, different optical channels 315 may be associated with the same or different sets of "candidate" measurement profiles 330.

While much of the present disclosure is described in the context of selecting measurement profiles 330 for different optical channels 315, this is not to be regarded as a limitation of the present disclosure, unless noted otherwise herein. In particular, techniques described herein may be used to select different measurement profiles 330 for other types of measurements/measurement channels, such as electrocardiogram (ECG) measurements, impedance cardiography (BioZ) signals, and the like. For example, in cases where a wearable device includes sensors for collecting BioZ data from a user, the wearable device 104 may be configured to test out different measurement profiles 330 for collecting BioZ signals, and may select which measurement profile 330 will be used for collecting subsequent BioZ signals.

Figure 4:
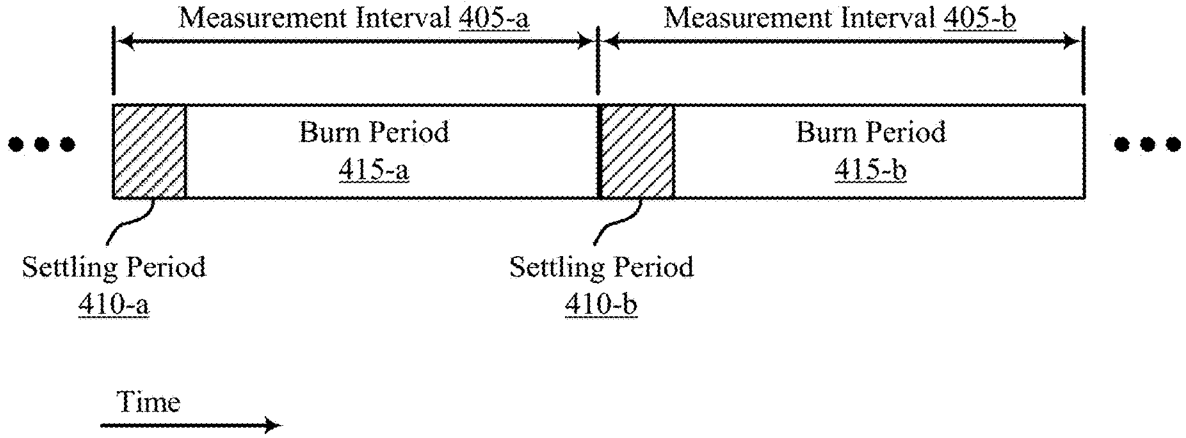
FIG. 4 illustrates an example of a measurement configuration that supports techniques for optimal parameter tuning for a wearable device in accordance with aspects of the present disclosure.

FIG. 4 illustrates an example of a measurement configuration 400 that supports techniques for optimal parameter tuning for a wearable device in accordance with aspects of the present disclosure. The measurement configuration 400 may implement, or be implemented by, aspects of the system 100, system 200, the system 300, or any combination thereof. For example, the measurement configuration 400 illustrates multiple measurement intervals 405, which may be examples of the measurement intervals 335 shown and described in FIG. 3.

As described previously herein, a wearable device 104 may perform physiological data measurements using optical channel 315 during different measurement intervals 405 (e.g., first measurement interval 405-*a*, second measurement interval 405-*b*). Each measurement interval 405 may include a settling period 410 (e.g., a silence period) and a burn period 415. For example, the first measurement interval 405-*a* may include a first settling period 410-*a* and a first burn period 415-*a*, and the second measurement interval 405-*b* may include a second settling period 410-*b* and a second burn period 415-*b*.

The settling periods 410 of the measurement intervals 405 may be associated time durations during which an LED of the optical channel 315 is not burning or otherwise emitting light (e.g., when the LED 310 is OFF). In such cases, the settling periods 410 may represent periods of time in which the photodetectors 305 are not actively receiving light from the LEDs 310, but are rather returning to a "baseline" signal level in preparation to receive light from the LEDs 310 during the subsequent burn period 415. Comparatively, the burn periods 415 of the measurement intervals 405 may represent periods of time that an LED is burning or otherwise emitting light (e.g., when the LED 310 is ON). In this regard, the burn periods 415 represent time durations that the LEDs 310 are emitting light, and the photodetectors 305 are actively receiving emitted light to acquire physiological data. For example, the wearable device 104 may acquire first physiological data during the first burn period 415-*a* (e.g., using the first measurement profile 330-*a*), and may acquire second physiological data during the burn period 415-*b* (e.g., using the second measurement profile 330-*b*).

In some cases, the user device 104 and/or the wearable device 104 may configure the measurement intervals 405 such that the settling periods 410 each last microseconds between the burn periods 415 of the measurement intervals 405 in order to prevent cross talk between signals collected during the measurement intervals 405. In other words, the duration of the settling periods 410 may be configured to reduce cross talk between sequential burn periods 415.

The measurement intervals 405 may be freely selected to burn the same, different, or a combination of light-emitting components (e.g., LEDs 310) of the wearable device 104. In some examples, the maximum quantity of measurement intervals 405 for an AFE associated with the wearable device 104 may be 9 measurement intervals 405/measurement slots. Alternatively, an AFE that includes hardware signal switch(es) may have an increased quantity of measurement intervals 405 (e.g., 18 measurement intervals, 27 measurement intervals, etc.).

Figure 5:
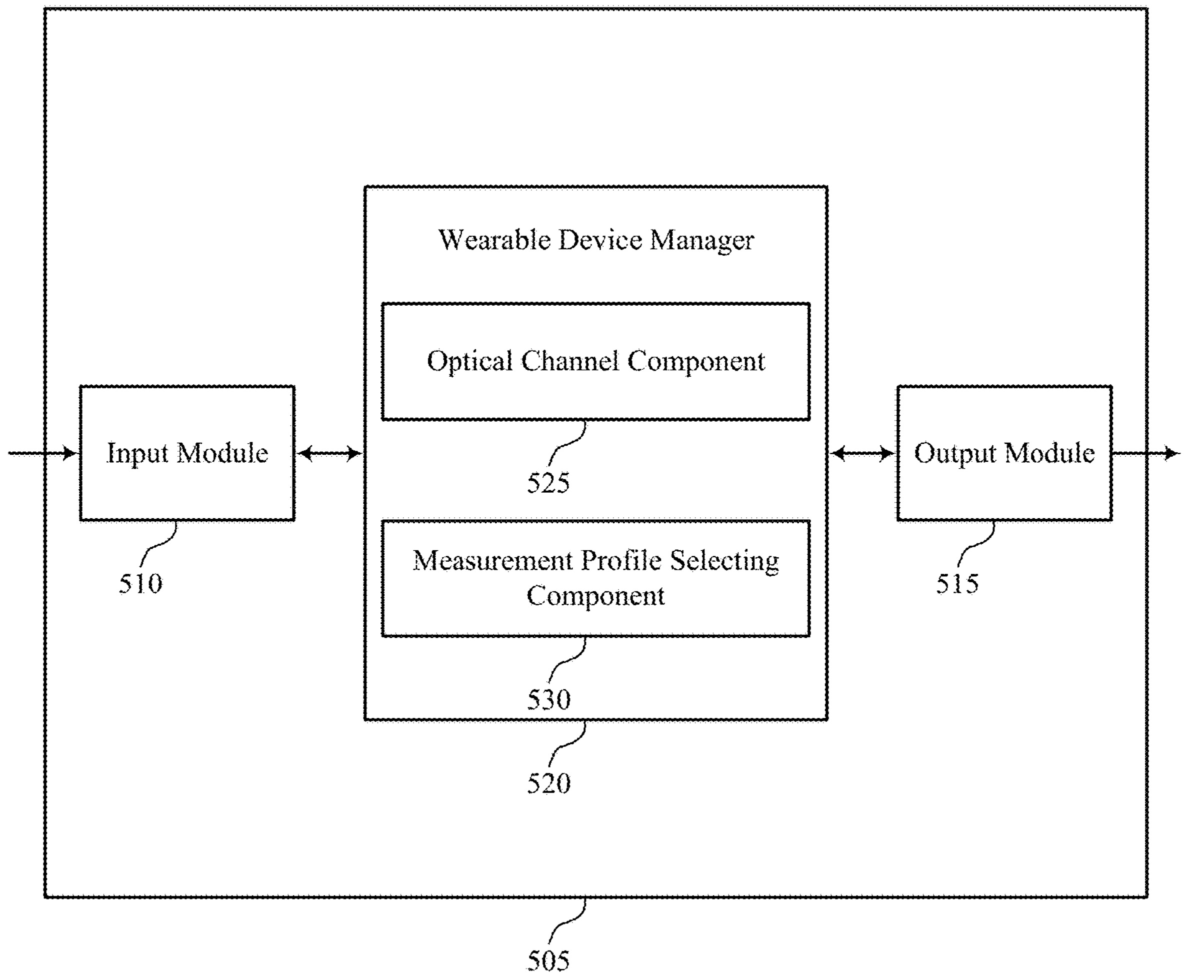
FIG. 5 shows a block diagram of an apparatus that supports techniques for optimal parameter tuning for a wearable device in accordance with aspects of the present disclosure.

FIG. 5 shows a block diagram 500 of a device 505 that supports techniques for optimal parameter tuning for a wearable device in accordance with aspects of the present disclosure. The device 505 may include an input module 510, an output module 515, and a wearable device manager 520. The device 505 may also include a processor. Each of these components may be in communication with one another (e.g., via one or more buses).

For example, the wearable device manager 520 may include an optical channel component 525 a measurement profile selecting component 530, or any combination thereof. In some examples, the wearable device manager 520, or various components thereof, may be configured to perform various operations (e.g., receiving, monitoring, transmitting) using or otherwise in cooperation with the input module 510, the output module 515, or both. For example, the wearable device manager 520 may receive information from the input module 510, send information to the output module 515, or be integrated in combination with the input module 510, the output module 515, or both to receive information, transmit information, or perform various other operations as described herein.

The optical channel component 525 may be configured as or otherwise support a means for acquiring first physiological data from a user during a first measurement interval using an optical channel of a wearable device, the optical channel comprising a light-emitting component and a photodetector, wherein the first physiological data is acquired using a first measurement profile. The optical channel component 525 may be configured as or otherwise support a means for acquiring second physiological data from the user during a second measurement interval using the optical channel of the wearable device, the second measurement interval subsequent to the first measurement interval, wherein the second physiological data is acquired using a second measurement profile. The measurement profile selecting component 530 may be configured as or otherwise support a means for selecting the first measurement profile or the second measurement profile based at least in part on a comparison of respective measurement quality metrics, respective power consumption metrics, or both, associated with the first measurement profile and the second measurement profile. The optical channel component 525 may be configured as or otherwise support a means for acquiring additional physiological data during a third measurement interval using the optical channel using the first measurement profile or the second measurement profile based at least in part on the selecting.

Figure 6:
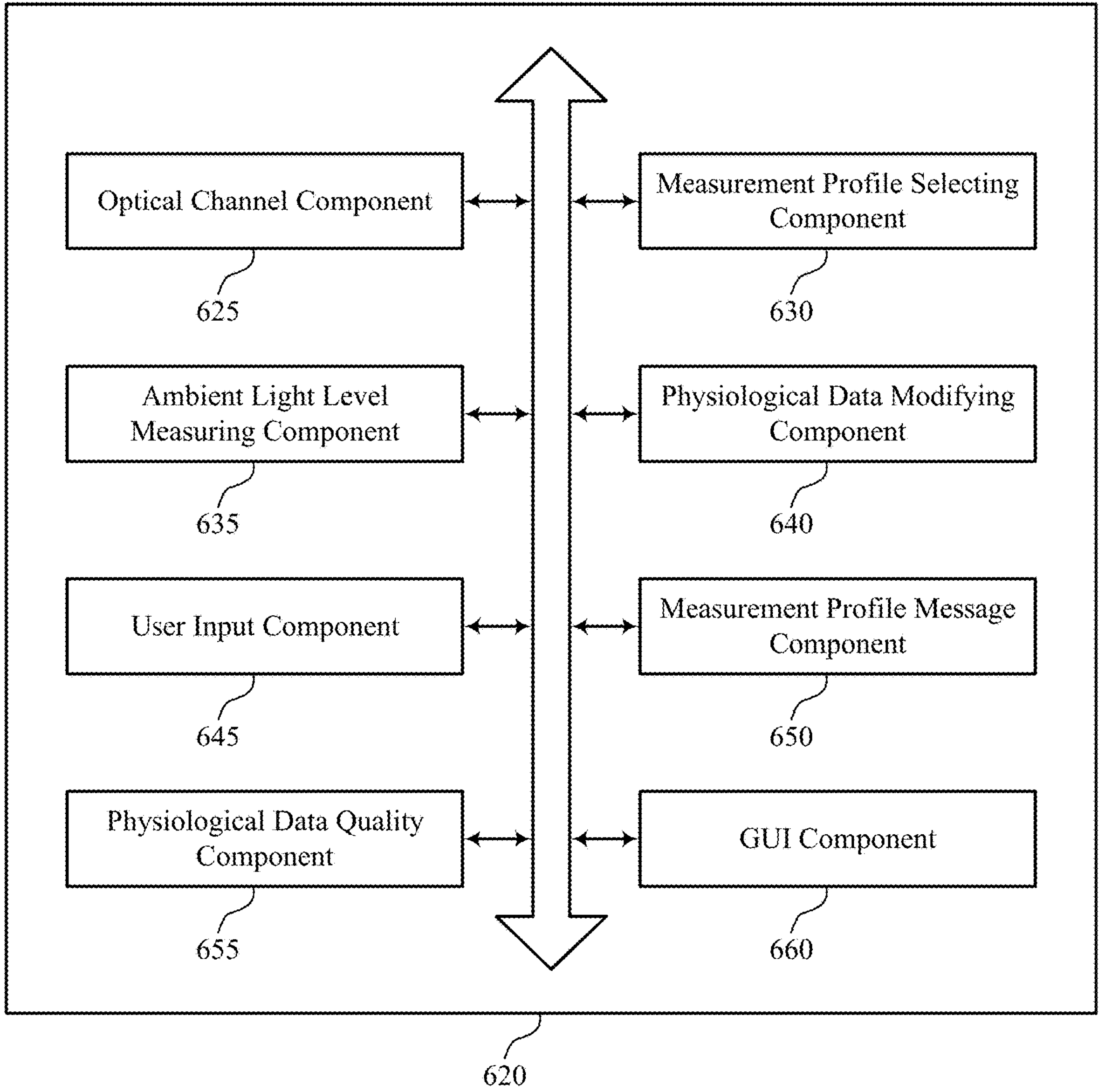
FIG. 6 shows a block diagram of a wearable device manager that supports techniques for optimal parameter tuning for a wearable device in accordance with aspects of the present disclosure.

FIG. 6 shows a block diagram 600 of a wearable device manager 620 that supports techniques for optimal parameter tuning for a wearable device in accordance with aspects of the present disclosure. The wearable device manager 620 may be an example of aspects of a wearable device manager or a wearable device manager 520, or both, as described herein. The wearable device manager 620, or various components thereof, may be an example of means for performing various aspects of techniques for optimal parameter tuning for a wearable device as described herein. For example, the wearable device manager 620 may include an optical channel component 625, a measurement profile selecting component 630, an ambient light level measuring component 635, a physiological data modifying component 640, a user input component 645, a measurement profile message component 650, a physiological data quality component 655, a GUI component 660, or any combination thereof. Each of these components may communicate, directly or indirectly, with one another (e.g., via one or more buses).

The optical channel component 625 may be configured as or otherwise support a means for acquiring first physiological data from a user during a first measurement interval using an optical channel of a wearable device, the optical channel comprising a light-emitting component and a photodetector, wherein the first physiological data is acquired using a first measurement profile. In some examples, the optical channel component 625 may be configured as or otherwise support a means for acquiring second physiological data from the user during a second measurement interval using the optical channel of the wearable device, the second measurement interval subsequent to the first measurement interval, wherein the second physiological data is acquired using a second measurement profile. The measurement profile selecting component 630 may be configured as or otherwise support a means for selecting the first measurement profile or the second measurement profile based at least in part on a comparison of respective measurement quality metrics, respective power consumption metrics, or both, associated with the first measurement profile and the second measurement profile. In some examples, the optical channel component 625 may be configured as or otherwise support a means for acquiring additional physiological data during a third measurement interval using the optical channel using the first measurement profile or the second measurement profile based at least in part on the selecting.

In some examples, the ambient light level measuring component 635 may be configured as or otherwise support a means for measuring a first ambient light level associated with the first measurement interval, and a second ambient light level associated with the second measurement interval. In some examples, the physiological data modifying component 640 may be configured as or otherwise support a means for modifying the first physiological data and the second physiological data based at least in part on the first ambient light level and the second ambient light level, respectively, wherein selecting the first measurement profile or the second measurement profile is based at least in part on the modifying.

In some examples, the first ambient light level, the second ambient light level, or both, comprise ambient light measurements at a beginning or end of the first measurement interval and the second measurement interval, respectively, average ambient light measurements throughout the first measurement interval and the second measurement interval, respectively, or any combination thereof.

In some examples, to support modifying the first physiological data and the second physiological data, the physiological data modifying component 640 may be configured as or otherwise support a means for subtracting the first ambient light level from a first signal generated by the photodetector during the first measurement interval. In some examples, to support modifying the first physiological data and the second physiological data, the physiological data modifying component 640 may be configured as or otherwise support a means for subtracting the second ambient light level from a second signal generated by the photodetector during the second measurement interval.

In some examples, the first measurement profile, the second measurement profile, or both, comprise one or more measurement parameters associated with the light-emitting component, the photodetector, or both, the one or more measurement parameters comprising a power level associated with the light-emitting component, a burn time associated with the light-emitting component, an analog-to-digital converter range associated with the photodetector, a tuning algorithm, or any combination thereof.

In some examples, the first measurement interval comprises a first settling period and a first burn period and. In some examples, the second measurement interval comprises a second settling period and a second burn period. In some examples, the first physiological data is acquired during the first burn period. In some examples, the second physiological data is acquired during the second burn period.

In some examples, the user input component 645 may be configured as or otherwise support a means for receiving, via a user device associated with the wearable device, a user input indicating an issue associated with physiological data collected by the wearable device. In some examples, the measurement profile message component 650 may be configured as or otherwise support a means for transmitting, to the wearable device based at least in part on the user input, a message indicating the first measurement profile and the second measurement profile, wherein acquiring the first physiological data, acquiring the second physiological data, or both, is based at least in part on the message.

In some examples, the measurement profile message component 650 may be configured as or otherwise support a means for receiving, from the wearable device, a message indicating which of the first measurement profile or the second measurement profile was selected.

In some examples, the physiological data quality component 655 may be configured as or otherwise support a means for determining that a quality of physiological data acquired by the wearable device via the optical channel fails to satisfy a quality threshold, wherein acquiring the first physiological data using the first measurement profile, acquiring the second physiological data using the second measurement profile, or both, is based at least in part on the determining.

In some examples, the GUI component 660 may be configured as or otherwise support a means for causing a GUI of a user device associated with the wearable device to display an indication of the additional physiological data.

In some examples, the optical channel component 625 may be configured as or otherwise support a means for acquiring third physiological data from the user using an additional optical channel of the wearable device, the additional optical channel comprising a second light-emitting component, a second photodetector, or both, wherein the third physiological data is acquired using a third measurement profile. In some examples, the optical channel component 625 may be configured as or otherwise support a means for acquiring fourth physiological data from the user using the additional optical channel, wherein the fourth physiological data is acquired using a fourth measurement profile. In some examples, the measurement profile selecting component 630 may be configured as or otherwise support a means for selecting the third measurement profile or the fourth measurement profile based at least in part on a comparison of respective measurement quality metrics, respective power consumption metrics, or both, associated with the third measurement profile and the fourth measurement profile. In some examples, the optical channel component 625 may be configured as or otherwise support a means for acquiring fifth physiological data using the additional optical channel using the third measurement profile or the fourth measurement profile based at least in part on selecting the third measurement profile or the fourth measurement profile.

In some examples, the wearable device comprises a plurality of optical channels. In some examples, each optical channel of the plurality of optical channels is associated with a set of candidate measurement profiles. In some examples, the set of candidate measurement profiles associated with the optical channel comprises the first measurement profile and the second measurement profile.

In some examples, the wearable device comprises a wearable ring device.

In some examples, the first physiological data, the second physiological data, or both, is acquired by the wearable device based on arterial blood flow, capillary blood flow, arteriole blood flow, or a combination thereof.

Figure 7:
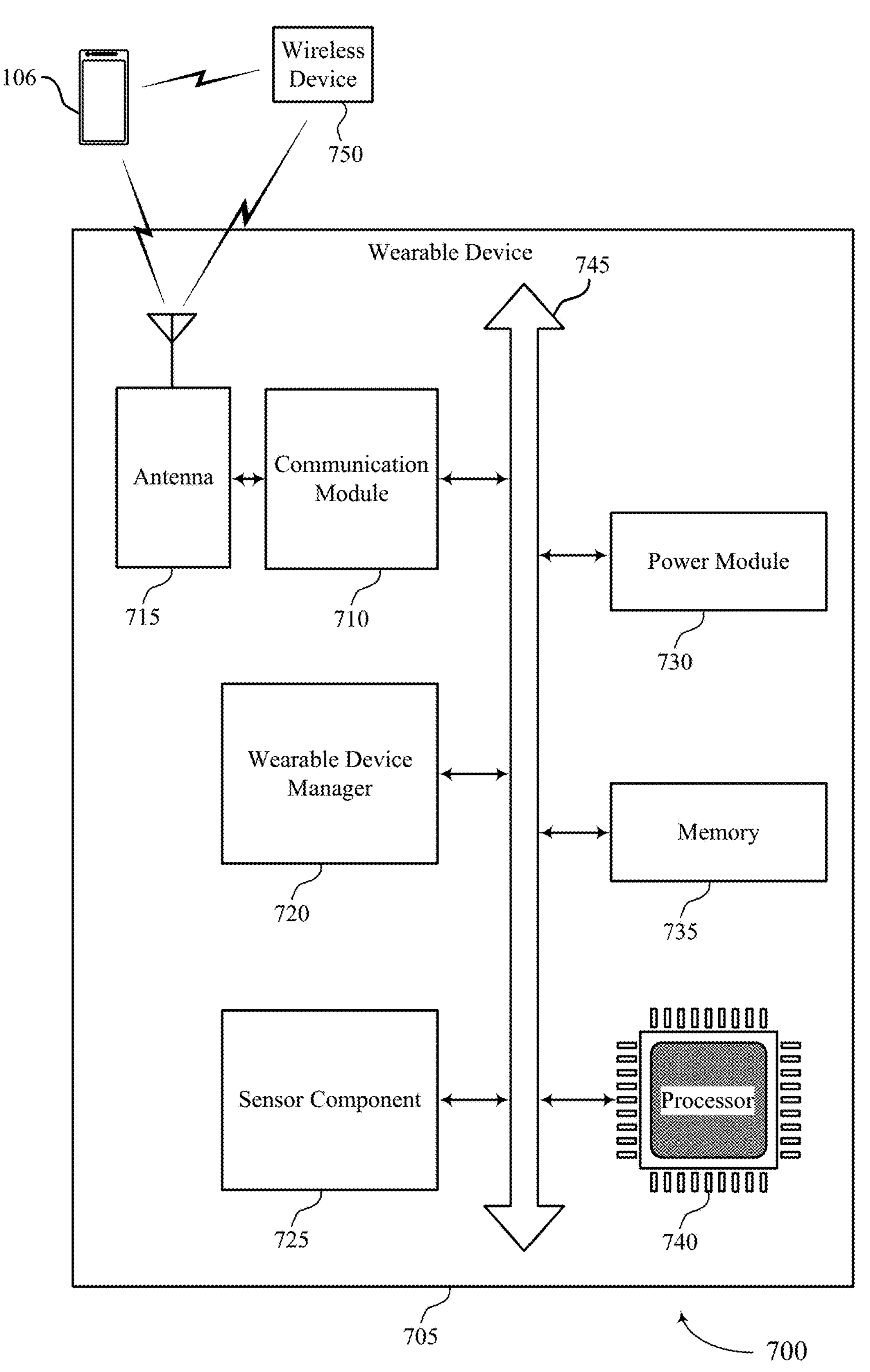
FIG. 7 shows a diagram of a system including a device that supports techniques for optimal parameter tuning for a wearable device in accordance with aspects of the present disclosure.

FIG. 7 shows a diagram of a system 700 including a device 705 that supports techniques for optimal parameter tuning for a wearable device in accordance with aspects of the present disclosure. The device 705 may be an example of or include the components of a device 505 as described herein. The device 705 may include an example of a wearable device 104, as described previously herein. The device 705 may include components for bi-directional communications including components for transmitting and receiving communications with a user device 106 and a server 110, such as a wearable device manager 720, a communication module 710, an antenna 715, a sensor component 725, a power module 730, a memory 735, a processor 740, and a wireless device 750. These components may be in electronic communication or otherwise coupled (e.g., operatively, communicatively, functionally, electronically, electrically) via one or more buses (e.g., a bus 745).

For example, the wearable device manager 720 may be configured as or otherwise support a means for acquiring first physiological data from a user during a first measurement interval using an optical channel of a wearable device, the optical channel comprising a light-emitting component and a photodetector, wherein the first physiological data is acquired using a first measurement profile. The wearable device manager 720 may be configured as or otherwise support a means for acquiring second physiological data from the user during a second measurement interval using the optical channel of the wearable device, the second measurement interval subsequent to the first measurement interval, wherein the second physiological data is acquired using a second measurement profile. The wearable device manager 720 may be configured as or otherwise support a means for selecting the first measurement profile or the second measurement profile based at least in part on a comparison of respective measurement quality metrics, respective power consumption metrics, or both, associated with the first measurement profile and the second measurement profile. The wearable device manager 720 may be configured as or otherwise support a means for acquiring additional physiological data during a third measurement interval using the optical channel using the first measurement profile or the second measurement profile based at least in part on the selecting.

By including or configuring the wearable device manager 720 in accordance with examples as described herein, the device 705 may support techniques for optimal parameter tuning for a wearable device, contributing to improved accuracy of physiological data measurement and reduced power consumption.

FIG. 8 shows a flowchart illustrating a method 800 that supports techniques for optimal parameter tuning for a wearable device in accordance with aspects of the present disclosure. The operations of the method 800 may be implemented by a wearable device or its components as described herein. For example, the operations of the method 800 may be performed by a wearable device as described with reference to FIGS. 1 through 7. In some examples, a wearable device may execute a set of instructions to control the functional elements of the wearable device to perform the described functions. Additionally, or alternatively, the wearable device may perform aspects of the described functions using special-purpose hardware.

At 805, the method may include acquiring first physiological data from a user during a first measurement interval using an optical channel of a wearable device, the optical channel comprising a light-emitting component and a photodetector, wherein the first physiological data is acquired using a first measurement profile. The operations of 805 may be performed in accordance with examples as disclosed herein. In some examples, aspects of the operations of 805 may be performed by an optical channel component 625 as described with reference to FIG. 6.

At 810, the method may include acquiring second physiological data from the user during a second measurement interval using the optical channel of the wearable device, the second measurement interval subsequent to the first measurement interval, wherein the second physiological data is acquired using a second measurement profile. The operations of 810 may be performed in accordance with examples as disclosed herein. In some examples, aspects of the operations of 810 may be performed by an optical channel component 625 as described with reference to FIG. 6.

At 815, the method may include selecting the first measurement profile or the second measurement profile based at least in part on a comparison of respective measurement quality metrics, respective power consumption metrics, or both, associated with the first measurement profile and the second measurement profile. The operations of 815 may be performed in accordance with examples as disclosed herein. In some examples, aspects of the operations of 815 may be performed by a measurement profile selecting component 630 as described with reference to FIG. 6.

At 820, the method may include acquiring additional physiological data during a third measurement interval using the optical channel using the first measurement profile or the second measurement profile based at least in part on the selecting. The operations of 820 may be performed in accordance with examples as disclosed herein. In some examples, aspects of the operations of 820 may be performed by an optical channel component 625 as described with reference to FIG. 6.

Figure 9:
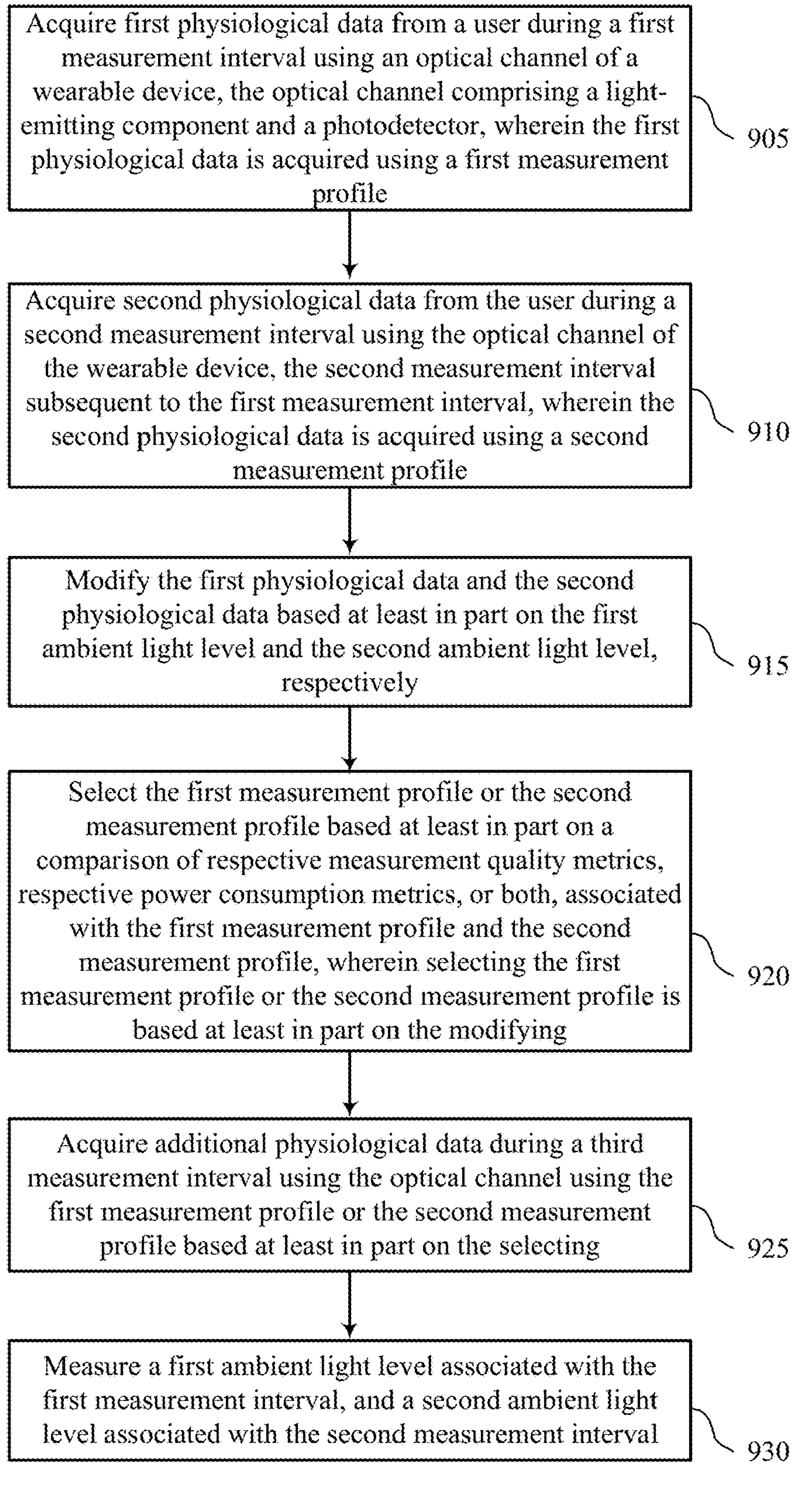

FIG. 9 shows a flowchart illustrating a method 900 that supports techniques for optimal parameter tuning for a wearable device in accordance with aspects of the present disclosure. The operations of the method 900 may be implemented by a wearable device or its components as described herein. For example, the operations of the method 900 may be performed by a wearable device as described with reference to FIGS. 1 through 7. In some examples, a wearable device may execute a set of instructions to control the functional elements of the wearable device to perform the described functions. Additionally, or alternatively, the wearable device may perform aspects of the described functions using special-purpose hardware.

At 905, the method may include acquiring first physiological data from a user during a first measurement interval using an optical channel of a wearable device, the optical channel comprising a light-emitting component and a photodetector, wherein the first physiological data is acquired using a first measurement profile. The operations of 905 may be performed in accordance with examples as disclosed herein. In some examples, aspects of the operations of 905 may be performed by an optical channel component 625 as described with reference to FIG. 6.

At 910, the method may include acquiring second physiological data from the user during a second measurement interval using the optical channel of the wearable device, the second measurement interval subsequent to the first measurement interval, wherein the second physiological data is acquired using a second measurement profile. The operations of 910 may be performed in accordance with examples as disclosed herein. In some examples, aspects of the operations of 910 may be performed by an optical channel component 625 as described with reference to FIG. 6.

At 915, the method may include modifying the first physiological data and the second physiological data based at least in part on the first ambient light level and the second ambient light level, respectively. The operations of 915 may be performed in accordance with examples as disclosed herein. In some examples, aspects of the operations of 915 may be performed by a physiological data modifying component 640 as described with reference to FIG. 6.

At 920, the method may include selecting the first measurement profile or the second measurement profile based at least in part on a comparison of respective measurement quality metrics, respective power consumption metrics, or both, associated with the first measurement profile and the second measurement profile, wherein selecting the first measurement profile or the second measurement profile is based at least in part on the modifying. The operations of 920 may be performed in accordance with examples as disclosed herein. In some examples, aspects of the operations of 920 may be performed by a measurement profile selecting component 630 as described with reference to FIG. 6.

At 925, the method may include acquiring additional physiological data during a third measurement interval using the optical channel using the first measurement profile or the second measurement profile based at least in part on the selecting. The operations of 925 may be performed in accordance with examples as disclosed herein. In some examples, aspects of the operations of 925 may be performed by an optical channel component 625 as described with reference to FIG. 6.

At 930, the method may include measuring a first ambient light level associated with the first measurement interval, and a second ambient light level associated with the second measurement interval. The operations of 930 may be performed in accordance with examples as disclosed herein. In some examples, aspects of the operations of 930 may be performed by an ambient light level measuring component 635 as described with reference to FIG. 6.

It should be noted that the methods described above describe possible implementations, and that the operations and the steps may be rearranged or otherwise modified and that other implementations are possible. Furthermore, aspects from two or more of the methods may be combined.

A method is described. The method may include acquiring first physiological data from a user during a first measurement interval using an optical channel of a wearable device, the optical channel comprising a light-emitting component and a photodetector, wherein the first physiological data is acquired using a first measurement profile, acquiring second physiological data from the user during a second measurement interval using the optical channel of the wearable device, the second measurement interval subsequent to the first measurement interval, wherein the second physiological data is acquired using a second measurement profile, selecting the first measurement profile or the second measurement profile based at least in part on a comparison of respective measurement quality metrics, respective power consumption metrics, or both, associated with the first measurement profile and the second measurement profile, and acquiring additional physiological data during a third measurement interval using the optical channel using the first measurement profile or the second measurement profile based at least in part on the selecting.

An apparatus is described. The apparatus may include a processor, memory coupled with the processor, and instructions stored in the memory. The instructions may be executable by the processor to cause the apparatus to acquire first physiological data from a user during a first measurement interval using an optical channel of a wearable device, the optical channel comprising a light-emitting component and a photodetector, wherein the first physiological data is acquired using a first measurement profile, acquire second physiological data from the user during a second measurement interval using the optical channel of the wearable device, the second measurement interval subsequent to the first measurement interval, wherein the second physiological data is acquired using a second measurement profile, select the first measurement profile or the second measurement profile based at least in part on a comparison of respective measurement quality metrics, respective power consumption metrics, or both, associated with the first measurement profile and the second measurement profile, and acquire additional physiological data during a third measurement interval using the optical channel using the first measurement profile or the second measurement profile based at least in part on the selecting.

Another apparatus is described. The apparatus may include means for acquiring first physiological data from a user during a first measurement interval using an optical channel of a wearable device, the optical channel comprising a light-emitting component and a photodetector, wherein the first physiological data is acquired using a first measurement profile, means for acquiring second physiological data from the user during a second measurement interval using the optical channel of the wearable device, the second measurement interval subsequent to the first measurement interval, wherein the second physiological data is acquired using a second measurement profile, means for selecting the first measurement profile or the second measurement profile based at least in part on a comparison of respective measurement quality metrics, respective power consumption metrics, or both, associated with the first measurement profile and the second measurement profile, and means for acquiring additional physiological data during a third measurement interval using the optical channel using the first measurement profile or the second measurement profile based at least in part on the selecting.

A non-transitory computer-readable medium storing code is described. The code may include instructions executable by a processor to acquire first physiological data from a user during a first measurement interval using an optical channel of a wearable device, the optical channel comprising a light-emitting component and a photodetector, wherein the first physiological data is acquired using a first measurement profile, acquire second physiological data from the user during a second measurement interval using the optical channel of the wearable device, the second measurement interval subsequent to the first measurement interval, wherein the second physiological data is acquired using a second measurement profile, select the first measurement profile or the second measurement profile based at least in part on a comparison of respective measurement quality metrics, respective power consumption metrics, or both, associated with the first measurement profile and the second measurement profile, and acquire additional physiological data during a third measurement interval using the optical channel using the first measurement profile or the second measurement profile based at least in part on the selecting.

Some examples of the method, apparatuses, and non-transitory computer-readable medium described herein may further include operations, features, means, or instructions for measuring a first ambient light level associated with the first measurement interval, and a second ambient light level associated with the second measurement interval and modifying the first physiological data and the second physiological data based at least in part on the first ambient light level and the second ambient light level, respectively, wherein selecting the first measurement profile or the second measurement profile may be based at least in part on the modifying.

In some examples of the method, apparatuses, and non-transitory computer-readable medium described herein, the first ambient light level, the second ambient light level, or both, comprise ambient light measurements at a beginning or end of the first measurement interval and the second measurement interval, respectively, average ambient light measurements throughout the first measurement interval and the second measurement interval, respectively, or any combination thereof.

In some examples of the method, apparatuses, and non-transitory computer-readable medium described herein, modifying the first physiological data and the second physiological data may include operations, features, means, or instructions for subtracting the first ambient light level from a first signal generated by the photodetector during the first measurement interval and subtracting the second ambient light level from a second signal generated by the photodetector during the second measurement interval.

In some examples of the method, apparatuses, and non-transitory computer-readable medium described herein, the first measurement profile, the second measurement profile, or both, comprise one or more measurement parameters associated with the light-emitting component, the photodetector, or both, the one or more measurement parameters comprising a power level associated with the light-emitting component, a burn time associated with the light-emitting component, an analog-to-digital converter range associated with the photodetector, a tuning algorithm, or any combination thereof.

In some examples of the method, apparatuses, and non-transitory computer-readable medium described herein, the first measurement interval comprises a first settling period and a first burn period and, the second measurement interval comprises a second settling period and a second burn period, the first physiological data may be acquired during the first burn period, and the second physiological data may be acquired during the second burn period.

Some examples of the method, apparatuses, and non-transitory computer-readable medium described herein may further include operations, features, means, or instructions for receiving, via a user device associated with the wearable device, a user input indicating an issue associated with physiological data collected by the wearable device and transmitting, to the wearable device based at least in part on the user input, a message indicating the first measurement profile and the second measurement profile, wherein acquiring the first physiological data, acquiring the second physiological data, or both, may be based at least in part on the message.

Some examples of the method, apparatuses, and non-transitory computer-readable medium described herein may further include operations, features, means, or instructions for receiving, from the wearable device, a message indicating which of the first measurement profile or the second measurement profile was selected.

Some examples of the method, apparatuses, and non-transitory computer-readable medium described herein may further include operations, features, means, or instructions for determining that a quality of physiological data acquired by the wearable device via the optical channel fails to satisfy a quality threshold, wherein acquiring the first physiological data using the first measurement profile, acquiring the second physiological data using the second measurement profile, or both, may be based at least in part on the determining.

Some examples of the method, apparatuses, and non-transitory computer-readable medium described herein may further include operations, features, means, or instructions for causing a GUI of a user device associated with the wearable device to display an indication of the additional physiological data.

Some examples of the method, apparatuses, and non-transitory computer-readable medium described herein may further include operations, features, means, or instructions for acquiring third physiological data from the user using an additional optical channel of the wearable device, the additional optical channel comprising a second light-emitting component, a second photodetector, or both, wherein the third physiological data may be acquired using a third measurement profile, acquiring fourth physiological data from the user using the additional optical channel, wherein the fourth physiological data may be acquired using a fourth measurement profile, selecting the third measurement profile or the fourth measurement profile based at least in part on a comparison of respective measurement quality metrics, respective power consumption metrics, or both, associated with the third measurement profile and the fourth measurement profile, and acquiring fifth physiological data using the additional optical channel using the third measurement profile or the fourth measurement profile based at least in part on selecting the third measurement profile or the fourth measurement profile.

In some examples of the method, apparatuses, and non-transitory computer-readable medium described herein, the wearable device comprises a plurality of optical channels, each optical channel of the plurality of optical channels may be associated with a set of candidate measurement profiles, and the set of candidate measurement profiles associated with the optical channel comprises the first measurement profile and the second measurement profile.

In some examples of the method, apparatuses, and non-transitory computer-readable medium described herein, the wearable device comprises a wearable ring device.

In some examples of the method, apparatuses, and non-transitory computer-readable medium described herein, the first physiological data, the second physiological data, or both, may be acquired by the wearable device based on arterial blood flow, capillary blood flow, arteriole blood flow, or a combination thereof.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. An apparatus, comprising:

a wearable device comprising a ring-shaped housing having an inner curved surface and an outer curved surface, wherein at least a portion of the inner curved surface is configured to contact a tissue of a user;

one or more processors;

one or more memories coupled with the one or more processors; and instructions stored in the one or more memories and executable by the one or more processors to cause the apparatus to:

acquire first physiological data from the user during a first measurement interval using an optical channel of the wearable device, the optical channel comprising a light-emitting component and a photodetector located at a first radial position and a second radial position, respectively, within the inner curved surface of the wearable device, wherein the first physiological data is acquired using a first measurement profile;

acquire second physiological data from the user during a second measurement interval using the optical channel of the wearable device, the second measurement interval subsequent to the first measurement interval, wherein the second physiological data is acquired using a second measurement profile;

select the first measurement profile or the second measurement profile based at least in part on a comparison of respective measurement quality metrics, respective power consumption metrics, or both, associated with the first measurement profile and the second measurement profile;

acquire additional physiological data during a third measurement interval using the optical channel using the first measurement profile or the second measurement profile based at least in part on the selecting; and input the additional physiological data into one or more machine learning classifiers to determine one or more metrics associated with the user.

2. The apparatus of claim 1, wherein the instructions are further executable by the one or more processors to cause the apparatus to:

measure a first ambient light level associated with the first measurement interval, and a second ambient light level associated with the second measurement interval; and modify the first physiological data and the second physiological data based at least in part on the first ambient light level and the second ambient light level, respectively, wherein selecting the first measurement profile or the second measurement profile is based at least in part on the modifying.

3. The apparatus of claim 2, wherein the first ambient light level, the second ambient light level, or both, comprise ambient light measurements at a beginning or end of the first measurement interval and the second measurement interval, respectively, average ambient light measurements throughout the first measurement interval and the second measurement interval, respectively, or any combination thereof.

4. The apparatus of claim 2, wherein the instructions to modify the first physiological data and the second physiological data are executable by the one or more processors to cause the apparatus to:

subtract the first ambient light level from a first signal generated by the photodetector during the first measurement interval; and subtract the second ambient light level from a second signal generated by the photodetector during the second measurement interval.

5. The apparatus of claim 1, wherein the first measurement profile, the second measurement profile, or both, comprise one or more measurement parameters associated with the light-emitting component, the photodetector, or both, the one or more measurement parameters comprising a power level associated with the light-emitting component, a burn time associated with the light-emitting component, an analog-to-digital converter range associated with the photodetector, a tuning algorithm, or any combination thereof.

6. The apparatus of claim 1, wherein the first measurement interval comprises a first settling period and a first burn period, and wherein the second measurement interval comprises a second settling period and a second burn period, wherein the first physiological data is acquired during the first burn period, and wherein the second physiological data is acquired during the second burn period.

7. The apparatus of claim 1, wherein the instructions are further executable by the one or more processors to cause the apparatus to:

receive, via the wearable device based at least in part on a user input associated with an issue with physiological data previously collected by the wearable device, a message indicating the first measurement profile and the second measurement profile, wherein acquiring the first physiological data, acquiring the second physiological data, or both, is based at least in part on the message.

8. The apparatus of claim 1, wherein the instructions are further executable by the one or more processors to cause the apparatus to:

communicate a message indicating which of the first measurement profile or the second measurement profile was selected.

9. The apparatus of claim 1, wherein the instructions are further executable by the one or more processors to cause the apparatus to:

determine that a quality of physiological data acquired by the wearable device via the optical channel fails to satisfy a quality threshold, wherein acquiring the first physiological data using the first measurement profile, acquiring the second physiological data using the second measurement profile, or both, is based at least in part on the determining.

10. The apparatus of claim 1, wherein the instructions are further executable by the one or more processors to cause the apparatus to:

cause a graphical user interface of a user device associated with the wearable device to display an indication of the additional physiological data.

11. The apparatus of claim 1, wherein the instructions are further executable by the one or more processors to cause the apparatus to:

acquire third physiological data from the user using an additional optical channel of the wearable device, the additional optical channel comprising a second light-emitting component, a second photodetector, or both, wherein the third physiological data is acquired using a third measurement profile;

acquire fourth physiological data from the user using the additional optical channel, wherein the fourth physiological data is acquired using a fourth measurement profile;

select the third measurement profile or the fourth measurement profile based at least in part on a comparison of respective measurement quality metrics, respective power consumption metrics, or both, associated with the third measurement profile and the fourth measurement profile; and acquire fifth physiological data using the additional optical channel using the third measurement profile or the fourth measurement profile based at least in part on selecting the third measurement profile or the fourth measurement profile.

12. The apparatus of claim 1, wherein the wearable device comprises a plurality of optical channels, where each optical channel of the plurality of optical channels is associated with a set of candidate measurement profiles, and wherein the set of candidate measurement profiles associated with the optical channel comprises the first measurement profile and the second measurement profile.

13. The apparatus of claim 1, wherein the wearable device comprises a wearable ring device.

14. The apparatus of claim 1, wherein the first physiological data, the second physiological data, or both, is acquired by the wearable device based on arterial blood flow, capillary blood flow, arteriole blood flow, or a combination thereof.

* * * * *